(12) United States Patent
Trifu et al.

(10) Patent No.: US 7,332,124 B2
(45) Date of Patent: Feb. 19, 2008

(54) ULTRAVIOLET DEVICE

(75) Inventors: Horea Gheorghe Trifu, Toronto (CA);
Jon N. Baswick, Burlington (CA);
Raymond L. R. Morrish, Ajax (CA);
Antonios Efantis, Don Mills (CA);
Faiek Dabiet, Thornhill (CA); Cynthia Desjardins, Toronto (CA); Douglas Pilch, Brampton (CA)

(73) Assignee: Miller Thomson, LLP, Toronto, Ontario (CA)

( * ) Notice: Subject to any disclaimer, the term of this patent is extended or adjusted under 35 U.S.C. 154(b) by 714 days.

(21) Appl. No.: 10/830,517

(22) Filed: Apr. 23, 2004

(65) Prior Publication Data

US 2005/0238531 A1  Oct. 27, 2005

(51) Int. Cl.
*A61L 9/00* (2006.01)

(52) U.S. Cl. .............................. 422/4; 422/24; 422/121

(58) Field of Classification Search ............... 422/4, 422/24, 121, 102; 313/318.01, 51, 49; 439/232, 439/282, 292, 226, 230, 235, 611
See application file for complete search history.

(56) References Cited

U.S. PATENT DOCUMENTS

| | | | |
|---|---|---|---|
| 5,334,347 A | 8/1994 | Hollander | |
| 5,436,817 A * | 7/1995 | Wotton et al. | 362/267 |
| 5,742,063 A | 4/1998 | Scroggins et al. | |
| 5,817,276 A | 10/1998 | Fencl et al. | |
| 5,835,840 A | 11/1998 | Goswami | |
| 5,866,076 A | 2/1999 | Fencl et al. | |
| 5,891,399 A | 4/1999 | Owesen | |
| 5,920,075 A | 7/1999 | Whitehead | |
| 6,179,969 B1 | 1/2001 | Larsen | |
| 6,194,731 B1 | 2/2001 | Jeys et al. | |
| 6,245,293 B1 | 6/2001 | Fencl et al. | |
| 6,267,924 B1 | 7/2001 | Fencl et al. | |
| 6,280,686 B1 | 8/2001 | Scheir et al. | |
| 6,313,470 B1 | 11/2001 | Fencl et al. | |
| 6,328,937 B1 | 12/2001 | Glazman | |
| 6,372,186 B1 | 4/2002 | Fencl et al. | |
| 6,423,882 B1 | 7/2002 | Fencl | |
| 6,500,267 B1 | 12/2002 | Fencl et al. | |
| 6,589,476 B1 | 7/2003 | Fencl | |
| 6,627,000 B2 | 9/2003 | Fencl et al. | |
| 6,746,134 B1 * | 6/2004 | Guzorek | 362/647 |

* cited by examiner

*Primary Examiner*—Walter D. Griffin
*Assistant Examiner*—Shanta G Doe
(74) *Attorney, Agent, or Firm*—Ohlandt, Greeley, Ruggiero & Perle, LLP

(57) ABSTRACT

A socket for a lamp comprising housing; a lamp holder displaceable relative said housing between an engaged and disengaged position; power cord associated with one of said housing; a lamp holder for powering said lamp in said engaged position; inhibiting displacement of said housing relative said lamp holder in said engaged position.

18 Claims, 11 Drawing Sheets

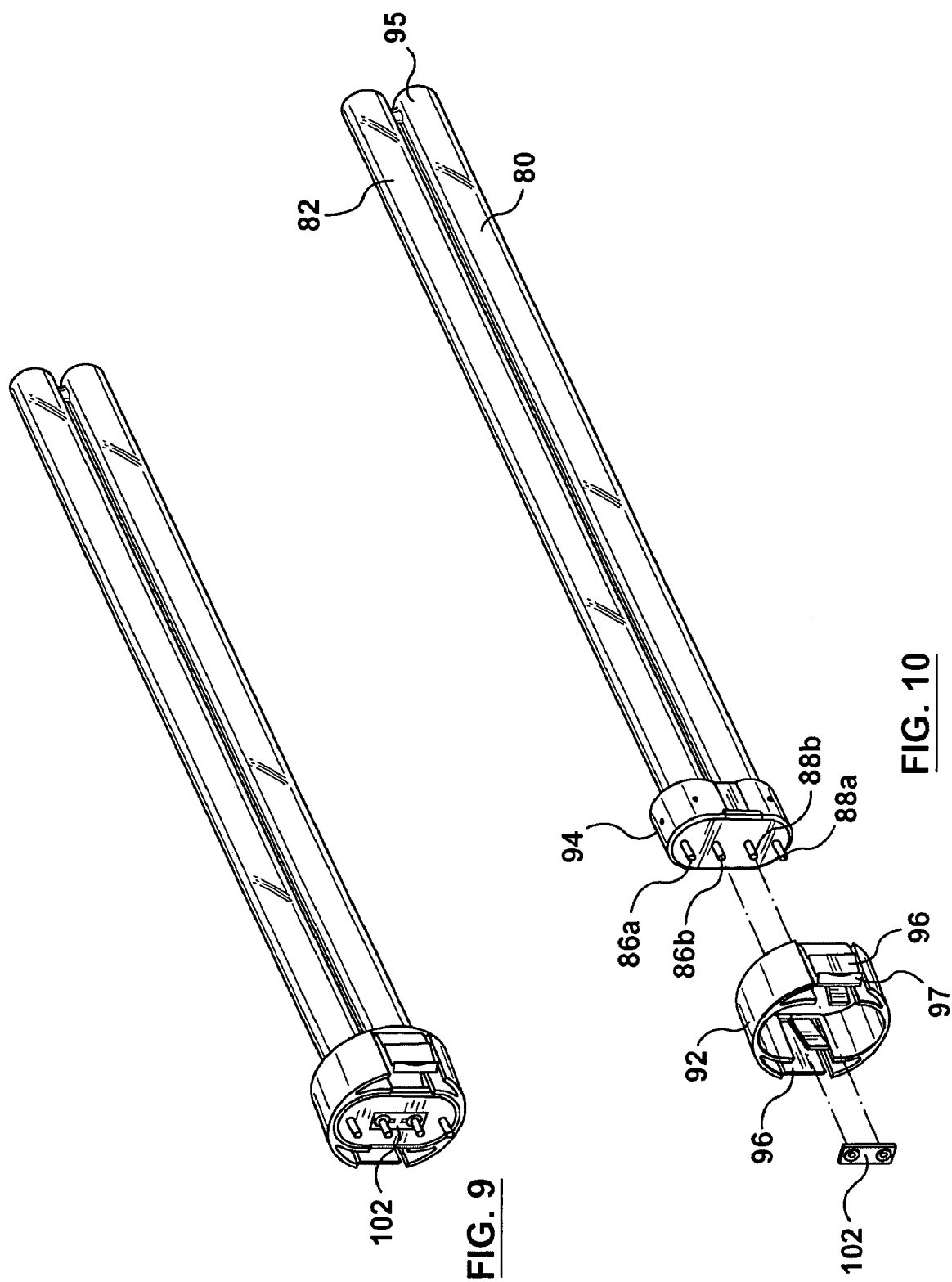

ULTRAVIOLET DEVICE

FIELD OF INVENTION

This invention relates generally to an assembly for a lamp, particularly to an assembly for a lamp that cannot be serviced without unplugging the power cord. The invention also relates to a device and method for purifying air in an air duct. Finally, the invention also relates to electrical circuitry for powering an ultraviolet lamp.

BACKGROUND TO THE INVENTION

Various devices and methods have heretofore been designed as sterilization devices, which include the use of ultraviolet radiation.

Ultraviolet radiation is a form of electromagnetic radiation that contains measurable wavelengths that have been known to be used for germicidal, bactericidal, and pathogenicidal effects.

For example, U.S. Pat. No. 6,194,731 B1 relates to biological aerosols being detected in real time by passing air, which may contain the aerosols, through a duct having a pair of photo detectors adjacent to the duct for detecting fluorescence of aerosols produced by ultraviolet laser beam illumination of the air flow.

Moreover U.S. Pat. No. 6,328,937 illustrates apparatus for killing micro-organisms in a primary flow of a fluid medium using germicidal beams to kill micro-organisms in a portion of the primary flow of the fluid medium which has a housing having an inlet and an outlet. The housing has reflective inner surfaces long the path of the germicidal beams at a source of the germicidal beams.

Furthermore, U.S. Pat. No. 6,179,969 B1 relates to a procedure and filter device for removal and destruction of organic substances in contaminated air.

Yet another device is illustrated in U.S. Pat. No. 5,891,399 which is used in an air purifying system. The device includes an ultraviolet radiation source, a pre-filter, and a post-filter. A pre-filter is arranged adjacent to the ultraviolet light source such that the pre-filter is irradiated by the ultraviolet light source to destroy bacteria, virus or other organisms on the pre-filter.

Furthermore, U.S. Pat. No. 5,835,840 relates to a photocatalytic system for air quality. Also, U.S. Pat. No. 5,742,063 shows a sterilizing unit for air ducts having an illuminating housing and at least one ultraviolet emitting probe extending downward into the duct. The upper surface of the unit overhangs the sidewalls for easy installation into the duct. At least one ultraviolet emitting probe in connection with the circuitry extends downward into the air duct. A light sensor extends from the upper side of the unit to a point near the probe in order to provide the visual indication of the condition of the ultraviolet probe without exposure to the ultraviolet light.

Finally, U.S. Pat. Nos. 5,920,075, 5,334,347, 5,866,076, 5,817,276, 6,372,186, 6,500,267, 6313,470, 6,245,293, 6,267,924, 6,280,686, 5,423,882, 6,859,476 and 6,627,000 relate to an ultraviolet sterilization device.

These prior devices and methods present relatively complicated structures.

It is an object of this invention to provide an approved device and method for sterilizing micro-organisms in fluid flow.

It is an aspect of this invention to provide an assembly for a lamp having a housing, a lamp holder displaceable relative to the housing between an engaged and disengaged position and a power cord associated with one of the housing or lamp holder for powering said lamp and inhibiting relative displacement of the housing and lamp.

It is another aspect of this invention to provide an ultraviolet lamp for purifying air, having a tube with two pairs of electrical pins and a fuse electrically connected to one of said pins in each of said pairs.

It is another aspect of this invention to provide an electrical circuit for powering an ultraviolet lamp having a fuse, comprising a controller for recognizing the fuse of the ultraviolet lamp, a counter for recording the duration of operation of the ultraviolet lamp, and said counter being reset upon insertion of a new ultraviolet lamp of said fuse, resuming said counter upon removal and reinsertion of the same ultraviolet lamp with said fuse, resuming the count upon power interruption with the same ultraviolet lamp and fuse, and continuing the count when the controller recognizes the fuse of said ultraviolet lamp.

It is another aspect of this invention to provide a method of purifying air in a ventilation duct from micro-organisms comprising the steps of; cutting an aperture in said duct; mounting a housing having a hole there through co-axially with said aperture, placing a lamp holder presenting an ultraviolet lamp into said aperture for extending said ultraviolet lamp into said duct, co-axially and rotationally displacing the lamp holder and lamp relative said housing to connect said lamp holder to said housing and cover said ultraviolet lamp in said duct, connecting a power cord in abutting relative relationship with its shoulder presented by said housing, electrically connecting the power cord to said lamp holder to power said ultraviolet lamp in said duct to purify said air, and inhibit displacement of said lamp holder relative said housing and prevent withdrawal of said lamp holder from said housing when said lamp is powered.

BRIEF DESCRIPTION OF DRAWINGS

These and other objects and features of the invention shall now be described in relation to the following drawings.

FIG. 9 is a perspective view of the ultraviolet lamp with the lamp socket.

FIG. 10 is an exploded view of FIG. 9.

FIGS. 11A, 11B, and 1C are circuit drawings of the invention.

DETAILED DESCRIPTION OF THE INVENTION

In the description that follows like parts are marked throughout the specification and drawings with the same respective numbers. The drawings are not necessarily to scale and in some instances proportions have been exaggerated in order to more clearly depict certain features of the invention.

Figure 1:
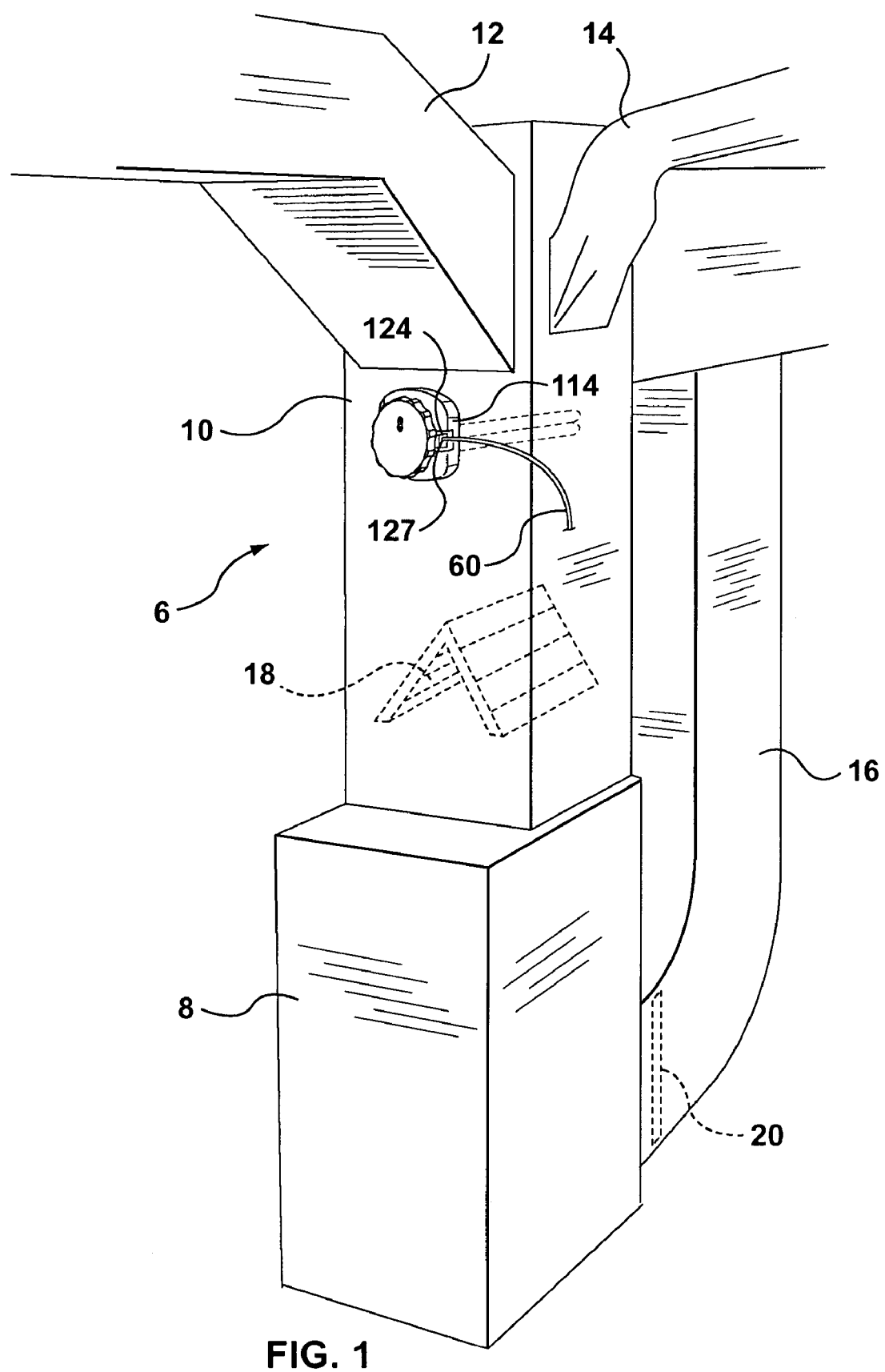
FIG. 1 is a perspective view of the ultraviolet light in an air duct system.
Figure 2:
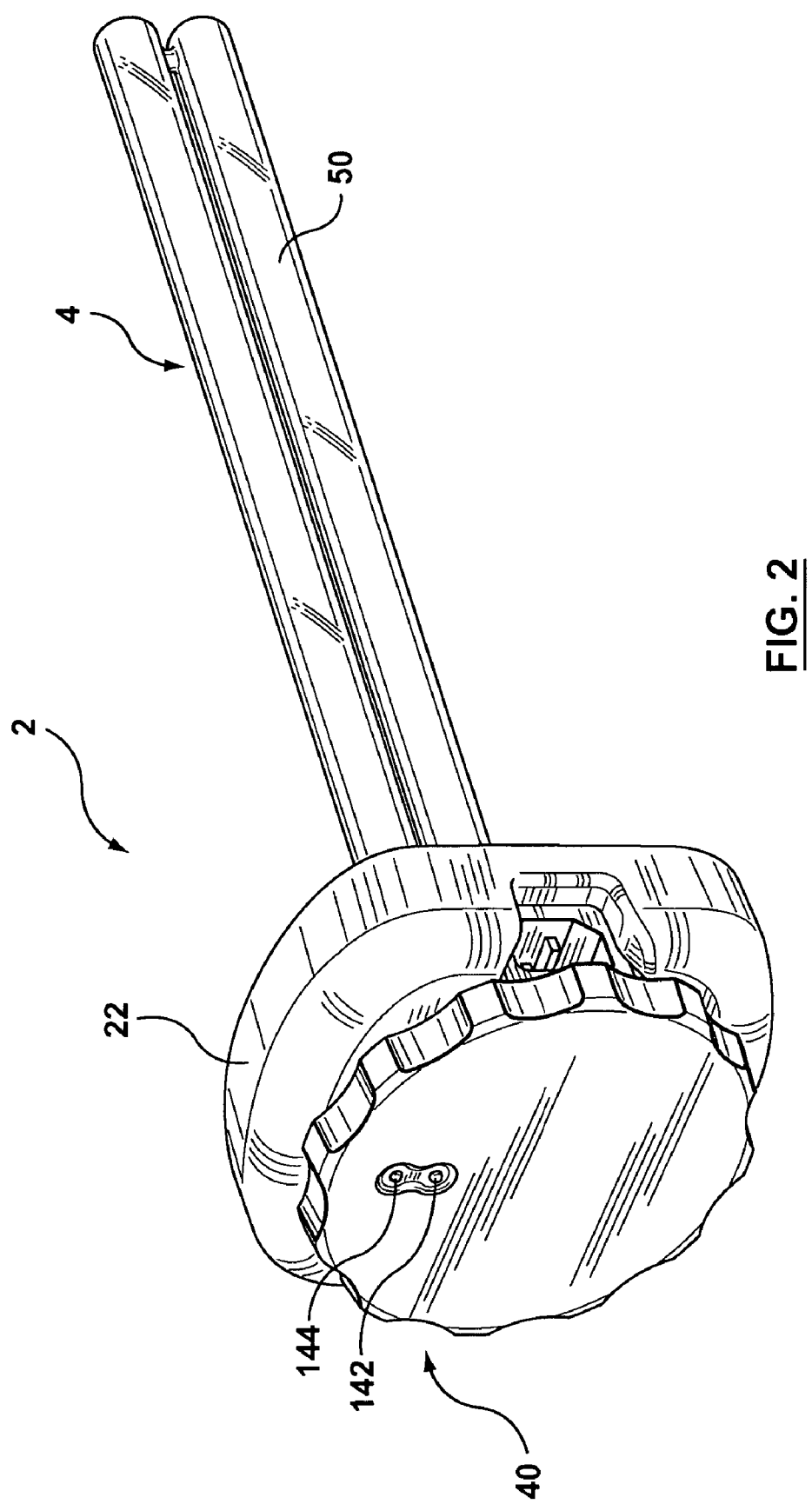
FIG. 2 is a perspective view of the assembly for the lamp.

FIGS. 1 and 2 illustrate a device 2 carrying an ultraviolet lamp for purifying air in a Heating Ventilating Air Conditioning System (HVAC). The HVAC system generally comprises a furnace 8 having heating or air conditioning ducts 10, 12 and 14 as well as a return air duct 16 all in the manner well known to those persons skilled in the art.

The device 2 can be mounted in the duct 10 above the air-conditioning coil 18, which is generally a breeding ground for micro-organisms in the wet or damp environment. Alternatively, the device 2 may be mounted in the return air duct 16 generally downstream of the air filter 20.

Generally speaking HVAC systems circulate either hot or air-conditioned air through the duct work in a circulatory fashion. Filters 20 are provided in a variety of positions in order to trap dust, pollutants in the circulated air. Generally speaking, bacteria, micro-organisms, can either pass through the filters or flourish in a moist atmosphere. The device 2 described herein is mounted in a duct system in order to reduce the percentage of micro-organisms or growth of bacteria or other pathogens by bathing the passing air with ultraviolet light.

Ultraviolet radiation is a form of electromagnetic radiation that has measurable wavelengths generally in the 4 to 400 nanometer range. The ultraviolet radiation utilized herein can be in the UV C output. In one embodiment, the radiation has a nanometer of 254, although, any wave length can be utilized in accordance with the invention described herein.

The device for the lamp 2 generally comprises housing 22, a lamp holder 40 for an ultraviolet lamp 50 as well as the power cord 60.

Figure 4:
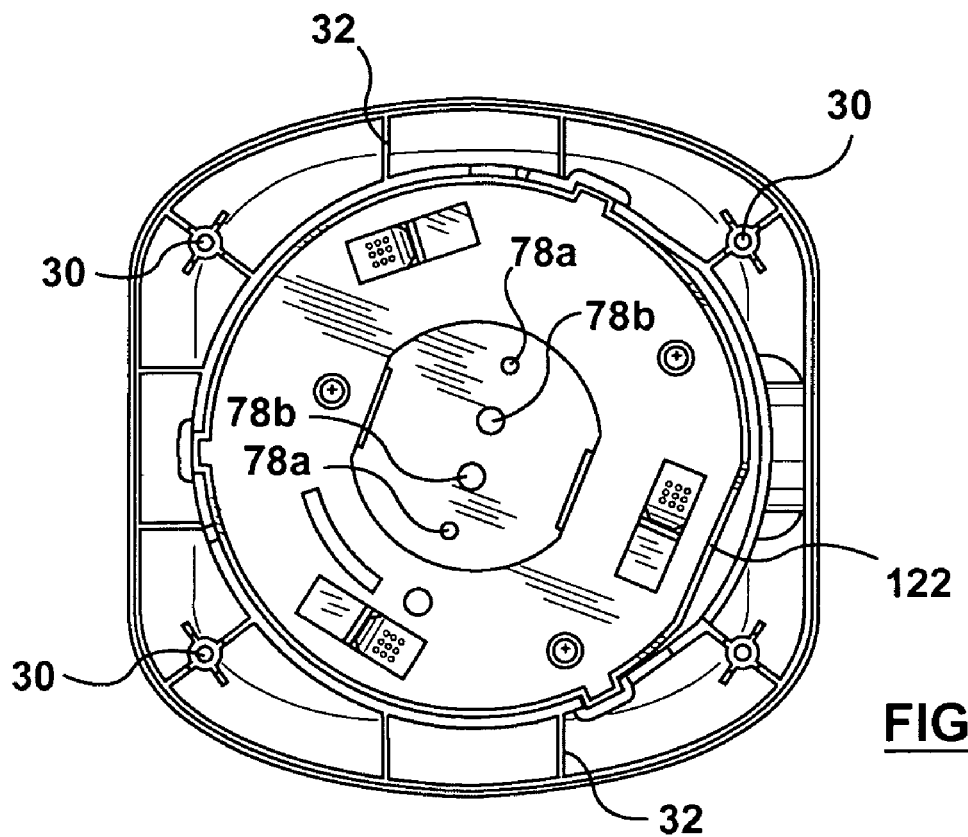
FIG. 4 is a back view of the case holder and case in a locked position.
Figure 4A:
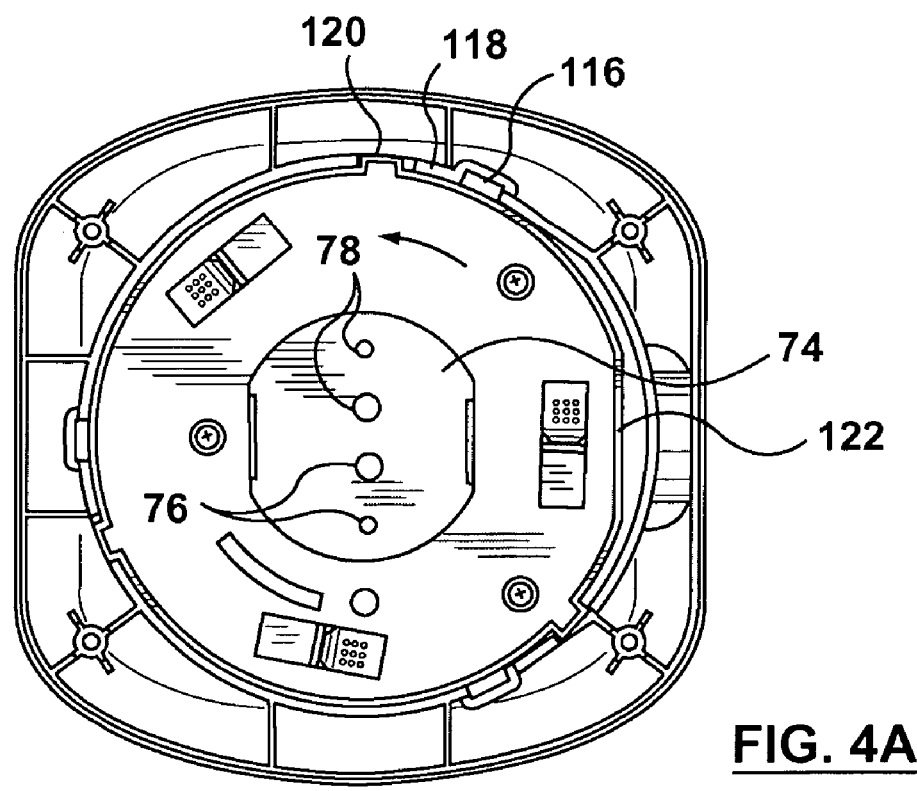
Figure 5:
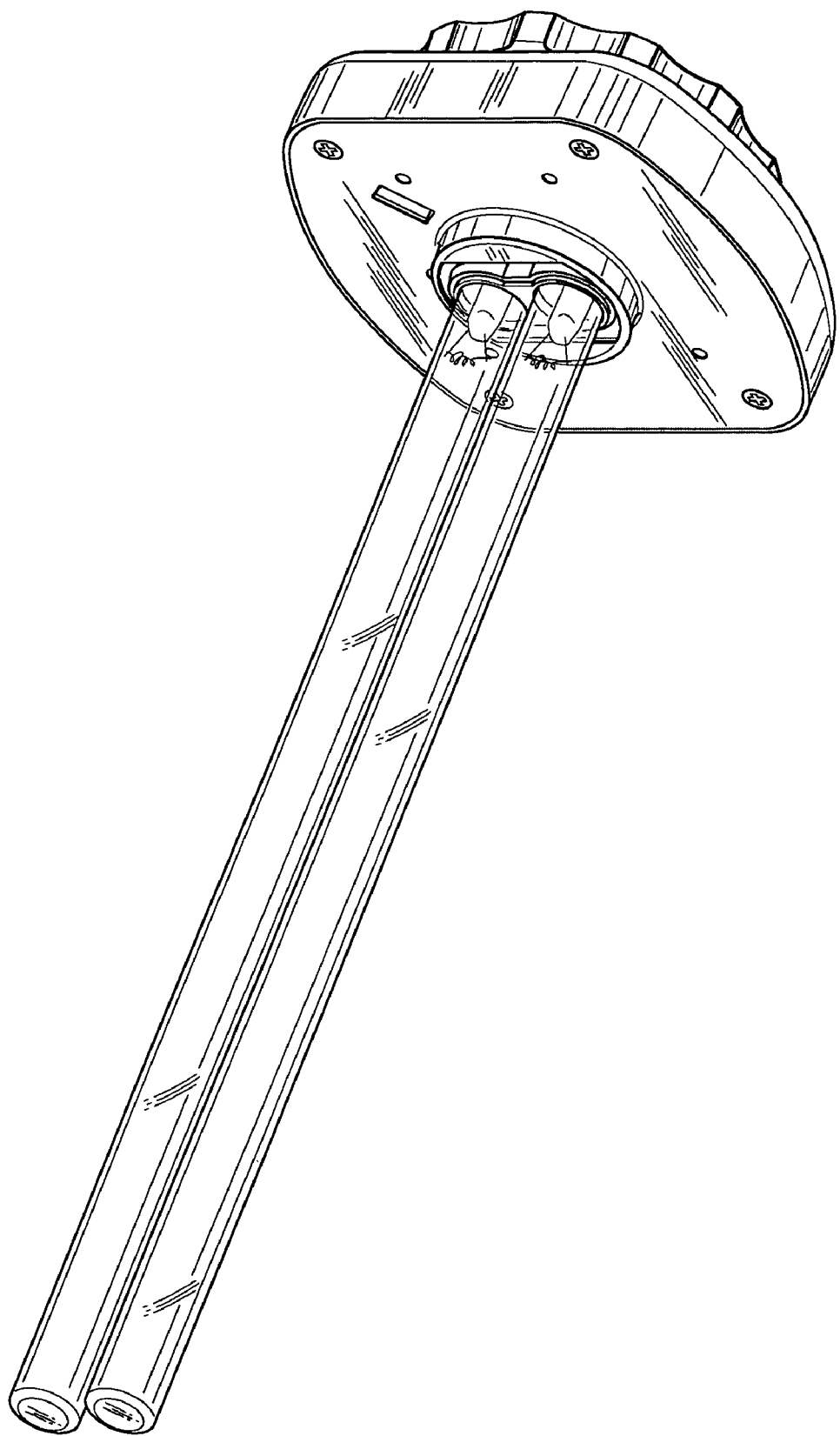
FIG. 5 is a perspective view of the assembly for the lamp taken from the point below the lamp assembly.

The lamp holder 40 is displaceable relative to the housing 22 between an engaged position shown in FIG. 4A and a disengaged position shown in FIG. 4 in a manner to be described herein. The power cord 60 is associated with one of the housing or lamp holders 22 and 40 respectively, for powering the ultraviolet lamp 50 as well as inhibiting relative displacement of the housing 22 and lamp holder 40 in a manner to be described herein.

The housing 22 generally comprises a case holder 24, and base plate 26. A base plate 26 has a plurality of base plate holes 28 adapted to receive a plurality of fasteners such as screws 30 for connecting the base plate 26 to the case holder 24 by fastening the screws 30 into the case holder posts 30 shown in FIG. 4. Generally speaking the case holder 24 can be hollow in one embodiment as shown in FIG. 4 having a plurality of reinforcing ribs 32.

The housing 22 includes a hole therethrough which comprises hole 34a through the case holder 24 and hole 34B through the base plate 26. The base plate hole 34b includes an annular flange 36 extending generally axially along axis 38.

The lamp holder 40 is comprised of a case 42 which registers with the case cover 44. The case 42 is generally hollow and comprises a generally circular end wall 46 having a slot 48 therein which is adapted to receive an engaging finger 52 upstanding from base plate 26. The circular end wall 46 presents an annular upstanding sidewall 54 having a cut-out 56 defining a shoulder 58 therein. The case 42 is adapted to receive the electrical circuitry (to be described below) within the confines or cavity 62 as defined by the circular end wall 46 and annular sidewall 54.

The case cover 44 includes a top surface 54 having a finger engaging knobs 66. The inner surface of the case cover 44 presents a plurality of alignment structures 68 for receiving case posts 70 which are adapted to receive a plurality of fasteners or screws 72 so as to secure the case 42 to the case cover 44.

The circular end wall 46 includes a socket recess 74 defined by socket bottom wall 73 and a circular peripheral wall 100. The socket recess 74 is adapted to receive a lamp socket 92 to be described herein. The socket recess 74 includes two pairs of pin holes 76 and 78 to receive two pairs of pins to be described herein. The ultraviolet lamp or tube 50 comprises the ultraviolet twin tubes which are joined together by glass bridging element 84 for communication between the tubes 80 and 82 in a manner well known to those persons skilled in the art.

The ultraviolet lamp 50 also includes a pair of pins 86a, 86b, and 88a and 88b. Pins 86a and 86b are connected to one of the filaments 84, while pins 88a and 88b are connected to the other filament 90. The ultraviolet lamp 50 includes the lamp socket 92 which can be connected to one end 94 of the ultraviolet lamp 50 by a variety of fastening means including gluing the lamp socket 92 to the lamp 50.

The lamp socket 92 includes a pair of movable or displaceable retaining clips 96 having engaging edges 97 adapted to be received by socket slots or openings 98 presented by the circular peripheral wall 100 of the socket recess 74. The pair of pins 86 and 88 are received by the pair of socket holes 76 and 78 such that pin 86a registers with socket hole 76a, 86b registers with socket hole 76b, and pin 88b registers with socket hole 78b, and pin 88a registers with socket hole 78a.

A printed circuit board (PCB) fuse 102 connects pins 86b and 88b as shown in FIGS. 10 and 9. The PCB fuse can be connected to the pins 86b and 88b by a variety of means including conductive glue so as to fix the PCB fuse to the pins thereto.

In operation the ultraviolet lamp 50 is manipulated so as to insert the one end 94 of the ultraviolet lamp 50 into the socket recess 74 whereby the engaging edges 97 will snap into the socket slots 98. The socket recess 74 can be adapted to receive a variety of ultraviolet lamps 50 and in the embodiment shown receives a lamp available from Philips.

In order to mount the housing 22 to the air ducts of the HVAC system a suitable aperture 114 is cut into the duct 10 for reception of the ultraviolet lamp 50 as shown in FIG. 1. Moreover, the base plate 26 includes a plurality of mounting holes 112 which are adapted to receive fasteners (not shown) so as to fasten the base plate to the duct 10. The annular flange 36 is received by the aperture 114 in the duct 10. The aperture will be sized to communicate with hole 34.

In the assembled housing 22, the hole 34a is much larger than hole 34b so as to permit mounting of the fasteners (not shown) through the mounting holes 112 so as to fasten the housing 22 on to the duct 10.

Thereafter, the lamp holder 40 with the lamp 50 is inserted such that the other end 95 of the lamp 50 is inserted through the hole 34 defined by hole 34a and 34b so that the other end 95 of the lamp is inserted internally of the duct 10 as shown in FIG. 1. The lamp holder 40 and housing 22 as well as the ultraviolet lamp 50 are co-axially disposed about axis 38 which is co-axially disposed relative aperture 114.

Figure 3:
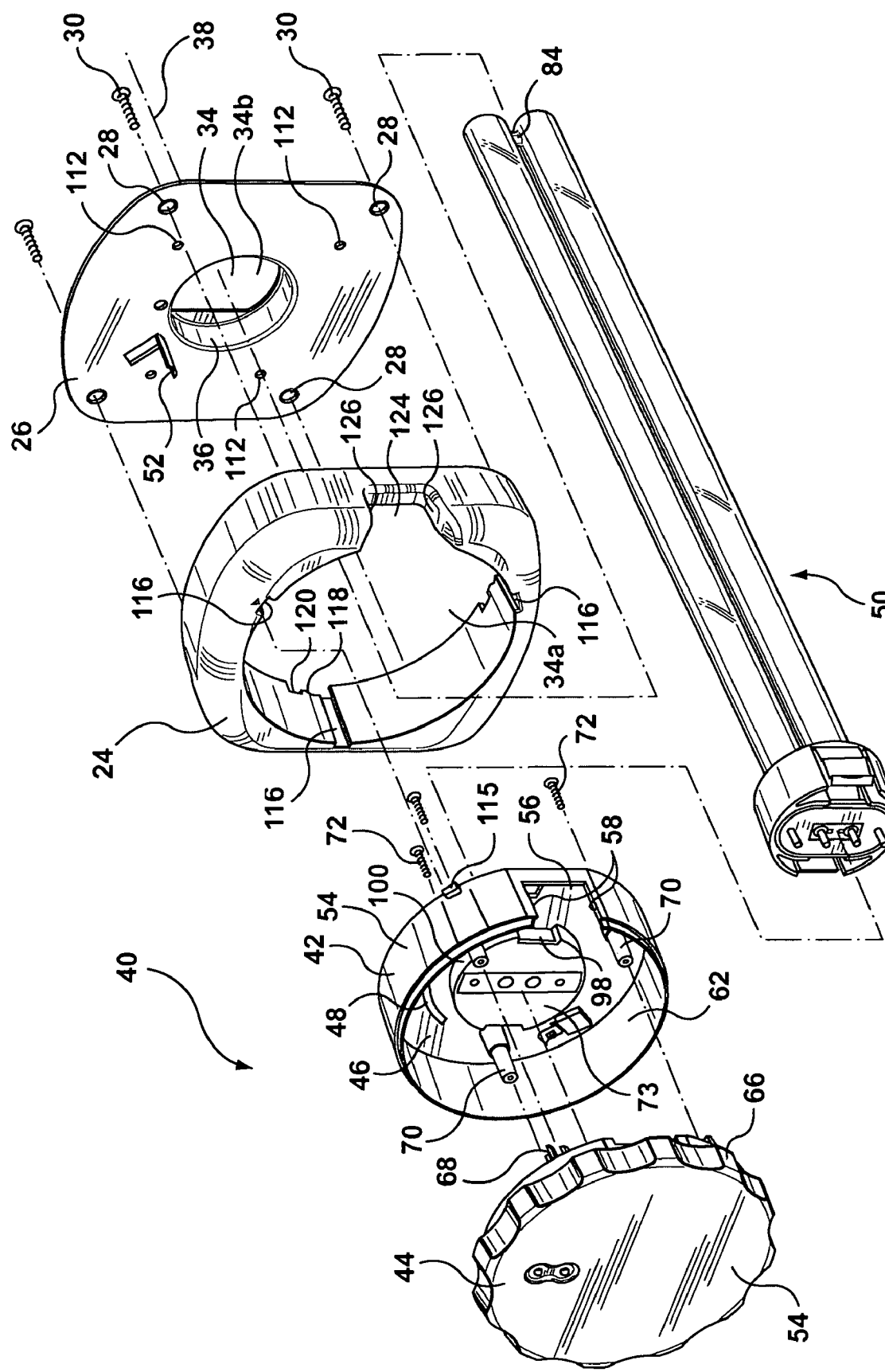
FIG. 3 is an exploded view of the assembly for the lamp.

More particularly, the annular sidewall 54 includes a plurality of aligning projections 115 which register housing 22 with the aligning slots 116. More specifically, the aligning projections 115 are axially received by the aligning slots 116 in a way so as to clear the slots 116. Thereafter, the lamp holder 40 can be rotationally displaced relative to the housing 22 so that the projections 115 ride over the sloped or arched cam surface 118 so as to slide into retaining slot 120. In particular the lamp holder 40 is rotating clockwise as shown in FIG. 3 or rotated counter-clockwise (the reverse) as shown in FIGS. 4 and 4A.

Figure 6:
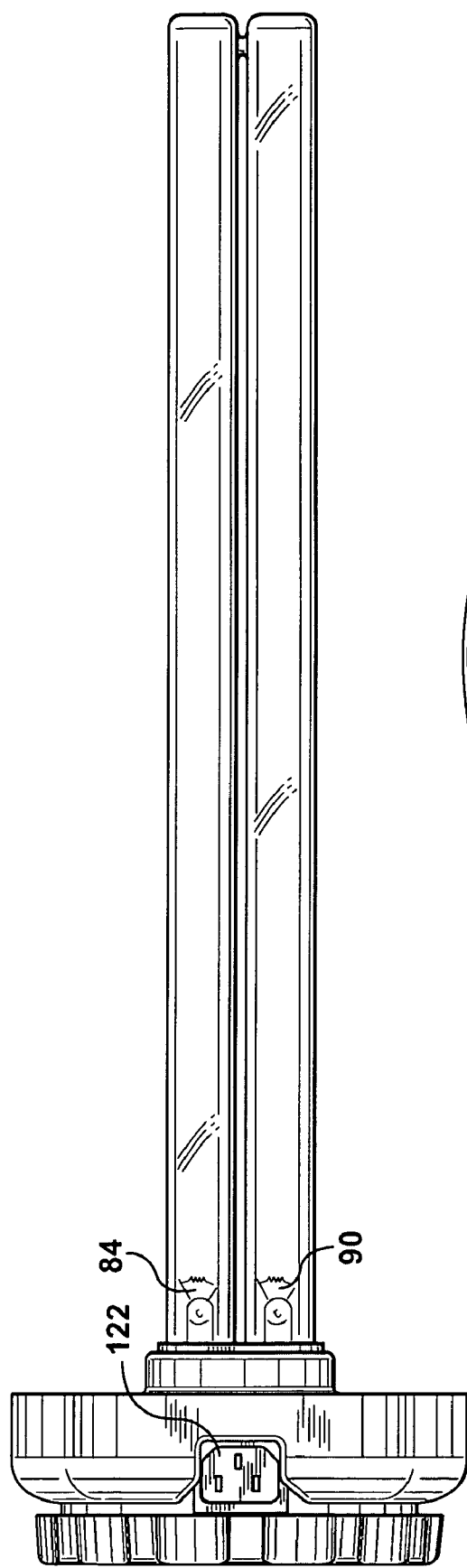
FIG. 6 is a side elevational view of the assembly for the lamp showing the power cord connection.
Figure 7:
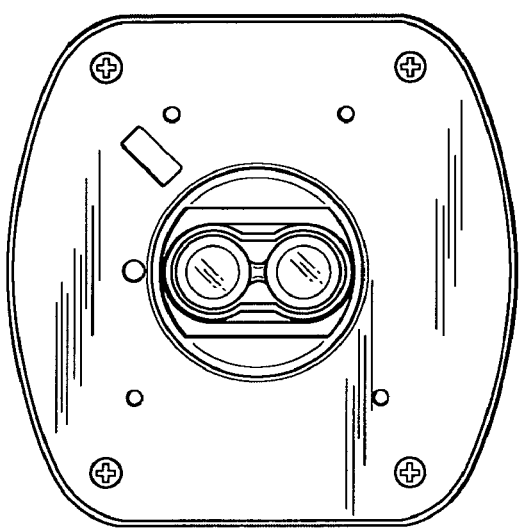
FIG. 7 is an end view taken from the left of FIG. 6.
Figure 8:
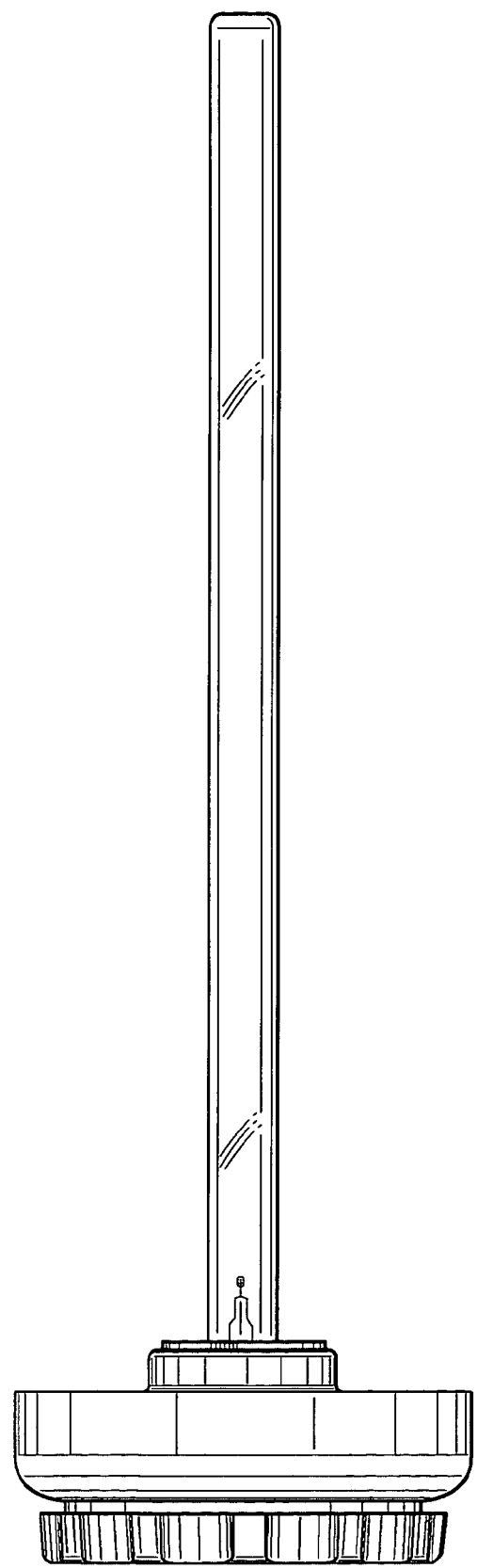
FIG. 8 is another side elevational view of FIG. 6.

The lamp holder 40 includes a female electrical receptacle 122 as best seen in FIGS. 2 and 6. More specifically, the female electrical receptacle 122 aligns with the male power cord receiving slot 124 of housing 22 as shown in FIG. 3. When the lamp holder 40 is rotationally engaged with the housing 22 in the locked position, the aligned projections 115 are received within retaining slots 120 and the power cord receiving slot 124 is aligned with the female receptacle 122 of the lamp holder 40. Once the male end of a power cord 127 into the cord receiving slot 124 to engage with female electrical receptacle 122 the shoulder 126 of the female power cord receiving slot 124 blocks or inhibits rotation of the lamp holder 40 relative to the housing 22. The lamp holder 40 is displaceable relative to housing 22 between an engaged position shown in FIG. 4a and a disengaged position shown in FIG. 4 whereby the lamp holder 40 with the lamp 50 can be withdrawn from the housing 22, without first disengaging the male end of the power cord 127 from the female power cord receiving slot 124.

The power cord 60 will only permit displacement of the lamp holder 40 relative to the housing 22 when the power cord is removed from the male receptacle of the lamp holder 40.

The lamp holder 40 includes the ultraviolet lamp 50, which is releasably secured to the lamp holder 40 for insertion of the ultraviolet lamp 50 through the hole 34 and aperture 114 to place or mount the ultraviolet lamp 50 into the air duct 10. The lamp holder 40 is rotatably displaced relative to the housing 22 between a closed position as shown in FIG. 4A locking the lamp holder 40 relative to the housing 22 and an unlocked position shown in FIG. 4 when the lamp holder 40 is removed from the housing 22 to permit removal of the lamp holder from the housing.

Accordingly, the ultraviolet lamp 50 may only be powered when the power cord 60 connects with the female receptacle 122. Furthermore the ultraviolet lamp may not be removed without withdrawing the power cord 60 from the female receptacle 122. This provides an added safety feature so that a person will not be exposed to the ultraviolet light as the ultraviolet lamp cannot be serviced without first disconnecting the power cord 60.

Figure 11A:
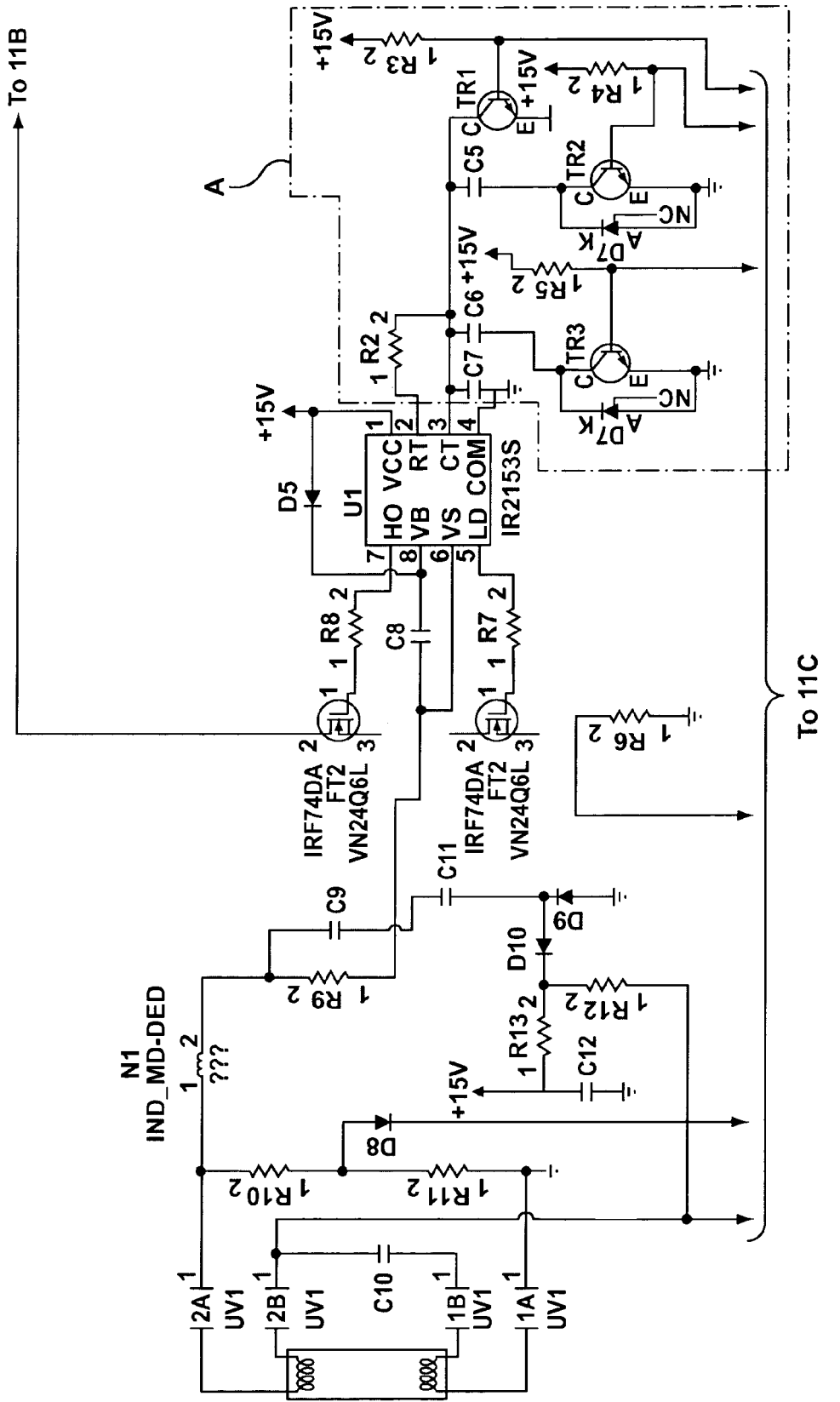
Figure 11B:
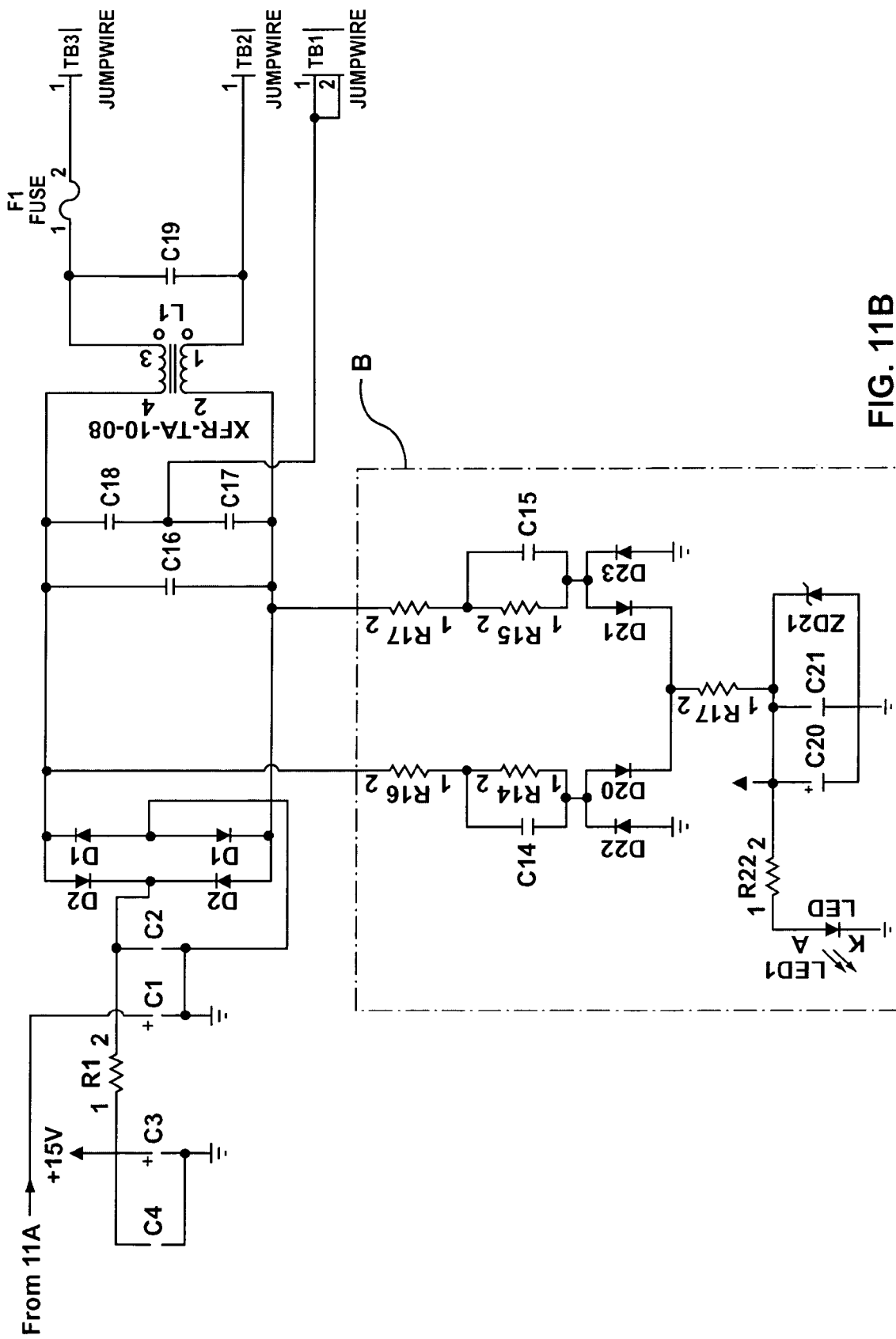
Figure 11C:
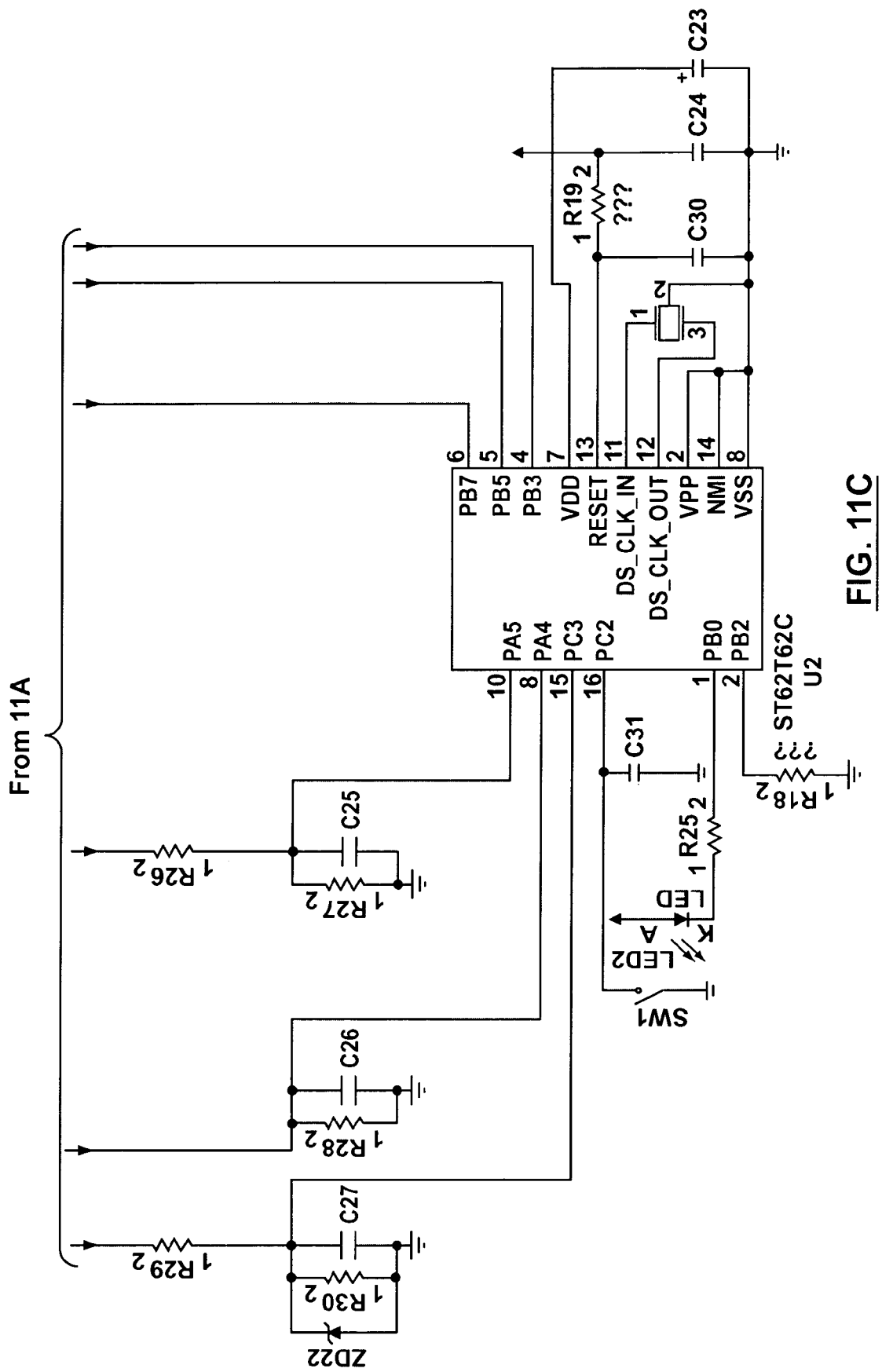

The lamp holder 40 also includes electrical circuitry as shown in FIG. 11.

In particular the pins 86a, 86b, 88b, 88a of UV lamp 50 register with pin receiving means UV1 as shown in FIG. 11A. Moreover, computer chip U1 contains the software and hardware interface with the ballast namely the half bridge inverter MOSFETS FT1 and FT2.

The lamp starting/control circuit is generally marked as A in FIG. 11A and comprises lamp shut down TR1, lamp running capacitor C5, lamp ignition capacitor C6, and lamp preheat capacitor C7. Furthermore the lamp current sensing circuit comprises resistors R6, R 26, R27 and capacitor C25.

The lamp voltage sensing circuit comprises resistors R10, R11, R28, capacitor C26 and D6. New lamp detection circuit comprises resistors R29, R30, capacitor C27 and 2022.

Capacitors C3 and C4 with resistor R1 comprise the power supply for the half bridge inverter MOSFET driver.

L1 comprises an EMI filter, which inhibits electromagnetic interference from being conducted to the supply. A standard 120 volt 60 hertz supply is provided at TB2 and TB3 with ground at TB1.

The circuit marked B in FIG. 11B provides the DC power for the microprocessor U2.

Moreover the microprocessor comprises the computer chip U2 which contains the firmware for the controller and counter logic. The microprocessor inputs are located on the left-hand side of U2 while the outputs are located on the right hand side. The integral counter will record the operating hours of the ultraviolet lamp 50. The counter U2 will be reset upon insertion of a brand new lamp 50 having the fuse 102. If the ultraviolet lamp 50 is removed and the same lamp is reinserted (for example for cleaning purposes) the counter will continue to count. If the electrical power is interrupted and the circuit is restarted with the same lamp, the hours will continue to be cumulative in the counter U2.

After a selected number of hours, for example 10,000 hours, a red LED will indicate that the lamp should be replaced by a solid light. A solid LED light protrudes through lamp holder 40 and is shown as LED 142. LED 144 signals that the power is on and is shown in FIG. 11 as LED 1. When the lamp 50 is replaced the counter will be reset. After the lamp has expired the LED 142 will become solid which indicates that the lamp must be replaced.

The lamp 50 includes the lamp fuse 102 which is mounted on the two middle pins 86b and 88b. The fuse amp rating is selected to meet the preheat current to burn the fuse successfully. The microprocessor U2 continuously checks the continuity between the two middle pins each time the system is powered on. The counter can only be reset when the continuity is verified. If an ultraviolet lamp is inserted which does not have the fuse the unit will not turn on.

A prong 52 extends through curved slot 48 and contacts a switch within the circuitry when the lamp holder 40 is in the locked position to enable the circuitry. When the lamp holder is in the unlocked position the prong 52 moves away from the switch and disables the circuitry. Alternatively a magnet mounted to the duct replaces the prong. The magnet interacts with a reed switch (replaces the micro switch) to identify that the unit has been mounted to the duct and can power on a prong 52. This further ensures that the unit will not be engaged unless mounted to the duct.

Various embodiments of the invention have now been described in detail. Since changes in and/or additions to the above-described best mode may be made without departing from the nature, spirit or scope of the invention, the invention is not to be limited to said details.

We claim:

1. A socket for a lamp comprising:
   (a) housing;
   (b) a lamp holder displaceable relative said housing between an engaged and disengaged position;
   (c) power cord;
      i) associated with one of said housing a lamp holder for powering said lamp in said engaged position;
      ii) inhibiting displacement of said housing relative said lamp holder in said engaged position.

2. A socket for a lamp as claimed in claim 1, wherein said lamp holder is displaceable relative said housing when said power cord is removed.

3. A socket for a lamp as claimed in claim 2 wherein said housing is adapted to be associated with an air duct, said housing including a hole for registry with an aperture disposed in said duct.

4. A socket for a lamp as claimed in claim 3 wherein said lamp holder includes an ultraviolet lamp releaseably secured to said lamp holder for:

(a) insertion of said ultraviolet lamp through said hole and said aperture to dispose said ultraviolet lamp into said air duct; and
(b) rotationally displacing said lamp holder relative said housing between a:
  (i) lock position locking said lamp holder relative said housing;
  (ii) an unlocked position permitting removal of said lamp holder from said housing.

5. A socket for a lamp as claimed in claim 4 wherein said hole and aperture are generally co-axially disposed and said lamp holder is co-axially and rotationally displaceable relative said housing.

6. A socket for a lamp as claimed in claim 5 wherein said power cord is removably connectable to said lamp holder.

7. A socket for a lamp as claimed in claim 6 wherein said lamp holder includes a cut-out for receiving said power cord when said power cord is connected to said lamp holder.

8. A socket for a lamp as claimed in claim 7 wherein in said cut-out presents a shoulder for inhibiting rotation of said lamp holder relative said housing to prevent removal of said lamp holder and said lamp from said air duct when said power cord is connected to said lamp holder.

9. A socket for a lamp as claimed in claim 8 wherein said lamp holder includes circuitry connected to said power cord.

10. A socket for a lamp as claimed in claim 9 wherein said circuitry includes a counter for counting the duration of operation of said ultraviolet lamp.

11. A socket for a lamp as claimed in claim 10 wherein said ultraviolet lamp includes a fuse.

12. A socket for a lamp as claimed in claim 11 wherein said ultraviolet lamp includes a pair of ultraviolet lamps having two pairs of pins and a fuse connected between said pairs of pins.

13. A socket for a lamp as claimed in claim 12 wherein said fuse is disposed on a printed circuit board.

14. A socket for a lamp as claimed in claim 13 wherein said counter is reset upon insertion of a new ultraviolet lamp.

15. A socket for a lamp as claimed in claim 14 wherein said counter continues to count said duration of operation of said ultraviolet lamp after said lamp is removed from said lamp holder and re-inserted into said lamp holder, and after said power is interrupted and restarted with the same ultraviolet lamp.

16. A socket for a lamp as claimed in claim 15 wherein said circuitry includes a counter for continuously verifying the electrical continuity of said fuse between said pins when said ultraviolet lamp is powered to prevent said ultraviolet lamp to operate and said counter to count said duration of operation of said lamp.

17. A socket for a lamp as claimed in claim 16 wherein said counter is reset upon insertion of a new ultraviolet lamp having a fuse.

18. A socket for a lamp as claimed in claim 11 wherein said fuse is selected to meet a preheat current to power said ultraviolet lamp.

* * * * *

UNITED STATES PATENT AND TRADEMARK OFFICE
CERTIFICATE OF CORRECTION

PATENT NO. : 7,332,124 B2
APPLICATION NO. : 10/830517
DATED : February 19, 2008
INVENTOR(S) : Horea Gheorghe Trifu et al.

Page 1 of 1

It is certified that error appears in the above-identified patent and that said Letters Patent is hereby corrected as shown below:

On the Title Page

Item (73) please correct "Miller Thomson, LLP" to read as "Allanson International Inc."

Signed and Sealed this
Fourth Day of June, 2013

Teresa Stanek Rea
*Acting Director of the United States Patent and Trademark Office*